United States Patent
Wu et al.

[19]

[11] Patent Number: 6,074,524
[45] Date of Patent: Jun. 13, 2000

[54] READILY DEFIBERED PULP PRODUCTS

[75] Inventors: Jian Wu; Hugh West, both of Seattle; Terry M. Grant, Auburn, all of Wash.

[73] Assignee: Weyerhaeuser Company, Tacoma, Wash.

[21] Appl. No.: 08/920,689

[22] Filed: Aug. 29, 1997

Related U.S. Application Data

[60] Provisional application No. 60/029,739, Oct. 23, 1996.

[51] Int. Cl.[7] .......................... D21H 17/63; D21H 17/67; D21H 17/68
[52] U.S. Cl. ...................... 162/100; 162/181.8; 428/375; 428/357; 241/28
[58] Field of Search ..................................... 162/111, 112, 162/181.8, 100; 428/375, 384, 364; 604/374, 355; 241/22, 24.19, 28

[56] References Cited

U.S. PATENT DOCUMENTS

| | | | |
|---|---|---|---|
| 3,935,363 | 1/1976 | Burkholder et al. | 428/281 |
| 3,998,690 | 12/1976 | Lyness et al. | 162/141 |
| 4,469,746 | 9/1984 | Weisman et al. | 428/289 |
| 4,952,278 | 8/1990 | Gregory et al. | 162/141 |
| 5,294,299 | 3/1994 | Zeuner et al. | 162/145 |
| 5,432,000 | 7/1995 | Young, Sr. et al. | 428/372 |
| 5,492,759 | 2/1996 | Eriksson et al. | 428/375 |
| 5,611,890 | 3/1997 | Vinson et al. | 162/111 |

FOREIGN PATENT DOCUMENTS

| | | | |
|---|---|---|---|
| 462918 | 7/1990 | Sweden | D21C 9/00 |
| WO 91/05108 | 4/1991 | WIPO | 428/375 |
| WO 96/31353 | 10/1996 | WIPO | 162/111 |

OTHER PUBLICATIONS

Martinis, S. et al. Absorption of liquids by dry fiber networks. TAPPI Annual Meeting, Chicago (1981).
Hercules Inc. Use of talc to make a hydrophobic low density air laid pad. *Research Disclosure*, p. 747, Nov. 1993. (Disclosure No. 35552).

*Primary Examiner*—Stanley S. Silverman
*Assistant Examiner*—Kevin Cronin

[57] ABSTRACT

The invention relates to cellulose fluff pulp products that are debondable into fluff with markedly lower energy input, to a process for making the products, and to absorbent products using the fluff. Most of the pulp products show no reduction in liquid absorbency rate from that of untreated fiber and significantly higher rates than pulps treated with the usual debonding agents. The products are made by adhering fine non-cellulosic particles to the fiber surfaces using a retention aid. The fiber is preferably treated with the retention aid in an aqueous suspension for a sufficient time so that the retention aid is substantively bonded with little or none left free in the water. The fine particulate additive is then added and becomes attached and uniformly distributed over the fiber surfaces with very little particle agglomeration occurring. The fiber is most usually not refined or only very lightly refined before sheeting. However, it may be significantly refined to produce a product having a very high surface area. Kaolin clay is a preferred particulate additive. The treated pulp may be mixed with other fibers before sheeting or after it is debonded into a fluff. The fluff is highly advantageous in the absorbent portions of personal care products such as diapers or sanitary napkins.

47 Claims, 9 Drawing Sheets

Untreated Fiber - 150X

Treated Fiber, 25% Clay - 150X

Untreated Fiber - 8000X

Treated Fiber, 25% Clay - 8000X

READILY DEFIBERED PULP PRODUCTS

This application claims priority from Provisional Application Ser. No. 60/029739, filed Oct. 23, 1996.

The invention is a modified wood pulp product especially useful for production of fluff intended for use as the absorbent layer in disposable diapers, sanitary napkins, and similar absorbent hygienic products. The product may be debonded from the sheet form into an absorbent fluff with significantly reduced fiberization energy being required when compared to untreated pulps. Static generation during fluffing is markedly reduced or eliminated. The fluff has a lower content of knots and has a water absorbency rate essentially equivalent to untreated fiber. The products may also be used in sheeted form, with or without admixture of other fibers, as an absorbent layer in disposable diapers, sanitary napkins, and similar hygienic products.

BACKGROUND OF THE INVENTION

Absorbent hygienic products employing fiberized wood pulp have been available for many years. However, the tonnage used for this purpose was relatively modest until the advent of disposable diapers, first for infants and later for incontinent adults. The advent of these products and their worldwide use created an explosion in demand. The basic product leaving the papermill is most usually termed a "fluff pulp". In the United States it is most typically a fully bleached southern pine kraft process pulp produced in relatively heavy caliper, high basis weight sheets. The product is rewound into continuous rolls for shipment to the customer. Since the sheeted product is intended to be later reprocessed into individual fibers, low sheet strength is desirable and typically little or no refining is used prior to sheeting. The requirements for surface uniformity and formation are similarly moderate.

At the customer's plant, the rolls are continuously fed into a device, such as a hammermill, to be reduced as much as reasonably possible to individual fibers. The fiberized product is generally termed a cellulose "fluff". This is then continuously air laid into pads for inclusion in the intended product. U.S. Pat. No. 3,975,222 to Mesek is exemplary of such a process.

There are a number of well recognized problems associated with production of cellulose fluff. The hammermills used for fluff production are very large energy consumers. Further, the fluff may contain significant numbers of fiber bundles usually termed knots or nits. More vigorous defiberizing can reduce the knot content but at the expense of considerable fiber breakage and a high resulting content of very fine dusty material. To offset this problem the pulp mill may add chemical debonders prior to sheet formation. These are usually cationic quaternary ammonium compounds with aliphatic substituents on the nitrogen atom that, in essence, coat the fibers with a hydrocarbon film and interfere with the natural hydrogen bonding tendency of cellulose fibers. A typical debonder might have the formula

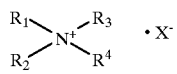

where $R_1$ and $R_2$ are long chain hydrocarbons or aliphatic polyether, $R_3$ and $R_4$ may be lower alkyl groups, and X is a salt forming anion. Examples of such compounds are seen in Canadian Patent 1,151,213 and Breese, U.S. Pat. No. 4,432,833. Debonders are effective for reducing energy consumption but create their own problem in the form of significantly poorer water absorption rates and somewhat lower water holding capacity. Considerable research has been expended on overcoming this problem; e.g., as exemplified in May et al., U.S. Pat. No. 4,425,186 and Laursen U.S. Pat. No. 4,303,471. However, as yet no fully satisfactory solution to the problem has been found. Manipulation during the papermaking process; e.g., by low or no wet end pressing or by using a higher headbox consistency can contribute only minimally to reduction in fiberization energy. Thus, there had been an unfilled need for a fluff pulp that can be fiberized with significantly lower energy input without losing the excellent water absorption rate of fluff made from an untreated pulp. The product of the present invention ably fills this need.

Lyness et al., in U.S. Pat. No. 3,998,690, separate a fiber stock into two portions. One is treated with an additive to make it cationic while the other is treated with an additive to make it more anionic. The portions are then recombined. The object is to cause flocculation in order to reduce loss of short fibers and fines. Clays are one of the materials said to increase the negative charge on the anionic portion.

Weisman et al., in U.S. Pat. No. 4,469,746, describe coating fibers with a continuous film of silica to improve hydrophilicity. The fibers themselves may be either a naturally hydrophilic material, such as cellulose, or a hydrophobic polymer such as polypropylene.

Jokinen et al., in U.S. Pat. No. 5,068,009 describe preparation of a cellulosic fluff pulp with improved fiberizing characteristics. This is made by treatment of the cellulose by a cellulolytic or hemicellulolytic enzyme at any time during the pulp making process.

Kobayashi et al., in U.S. Pat. No. 5,489,469, describe a liquid absorbent composite product in which water insoluble hydrophilic fibers and a water insoluble inorganic material are embedded into the surface of water absorbent polymer granules, such as a superabsorbent polymer. The inorganic material is chosen from a broad spectrum which includes alumina, silica, talc, clays, and many others. The fibers may be cellulosic. A sheeted pulp product is apparently not contemplated by these inventors.

Eriksson et al., in U.S. Pat. No. 5,492,759 describe methods of adhering hydrophilic inorganic chemicals to fiber surfaces for production of fluff pulps. Aluminum and iron compounds are suggested. The hydrophilic layer results in a decrease in contact angle and an increase in absorption rate.

Swedish Patent Application 8300460-6 describes making an easily debonded pulp by removal of at least 75% of the fines fraction that would pass through a 200 mesh screen. Up to 20–30% of the furnish is removed prior to and during sheet formation.

Swedish Patent No. 462,918 describes an easily debonded fluff pulp made by depositing very finely ground high alpha cellulose particles on the primary fibers. The particles act as spacers between fibers and prevent strong hydrogen bonding between adjacent fibers.

Chauvette et al., in U.S. Pat. No. 5,562,649 describe a flexible absorbent pulp sheet made by incorporating a debonder and then perf-embossing the product. The material may be used as is as an absorbent layer in absorbent hygienic products.

Vinson et al., in U.S. Pat. No. 5,611,890, describe a low dusting tissue product, useful as bath or facial tissue, which incorporates a particulate filler such as kaolin clay as a softening agent.

Research Disclosure Abstract 93355052 (1993) describes air-laid pads made from talc treated wood pulp useful as oil absorbent products or as a hydrophobic low density pad used as cover stock for diapers or other absorbent products. The talc is said to be distributed in the pad as aggregates, submicron particles, or as coatings on the fibers.

It is common practice to use talc in papermaking in very low percentages; e.g., <1%, as a pitch absorbent.

Mineral fillers have long been used in paper manufacture to lower costs and improve surface smoothness and printing properties. Internal usage may vary from as low as about 3% in products such as newsprint to as high as 30% or greater in magazine stock. This internal use must be differentiated from the use of surface coatings that may also have a high content of mineral products. In common with cellulose fibers, most fillers have a negative surface charge. Thus, filler particles and fibers generally tend to repel each other unless some chemical material is used as a retention aid. Without such an aid fillers are primarily retained by filtration in the web as it is dewatered on the forming wire and, since individual filler particles typically have an average equivalent spherical diameter of only about 1 $\mu$m or less, loss into the white water is usually quite high.

Retention aids are primarily charge modifiers. They may be anionic or nonionic but are much more usually cationic materials. Depending on their manner of use, retention aids can act by making the fibers cationic or less anionic, or the filler cationic or less anionic, so there is an electrostatic attraction between filler particles and fibers. More generally the retention aids are very high molecular weight cationic water soluble polymers that act as polyelectrolytes. As such, they act as bridges linking filler particles to fibers. Typically they are polyacrylamides, polyanines, polyethyleneimines, polyamidoamines, or polyethylene oxides.

Retention aids can act in a number of ways besides charge control to increase filler retention. They can be used to attract individual filler particles to the fiber surfaces for opacity improvement More usually they are used in a manner that will cause flocculation of fillers with themselves or with fibrils and fiber fines so that the effective particle size is very significantly increased. As such, the flocs are much more effectively retained by filtration within the interstices of the dewatering sheet.

Fillers affect paper sheet properties in several ways. Strength, particularly burst and tensile strength, may be reduced. Opacity, brightness, surface smoothness, and ink holdout are usually increased. Particles primarily adhered to the fiber surfaces interfere with fiber-to-fiber bonding. This increases the opacity due to the increased interfacial area that causes a higher proportion of incident or transmitted light to be scattered.

Although there are exceptions, in general papermaking practice it is usually most desirable to encourage filler flocculation so that the filler is predominantly retained in the interfiber spaces rather than on the fiber surfaces. This is done in part to minimize strength loss from use of the filler. Papers are normally rather highly refined to develop strength and ensure excellent formation. However, never before, to the present inventors' knowledge, have mineral fillers been used in conjunction with fluff pulps, which may be either refined-or unrefined, in order to deliberately effect strength loss so as to reduce debonding energy.

SUMMARY OF THE INVENTION

The present invention is a cellulosic fluff pulp product and the method of its manufacture. The product can be converted from sheeted form into individual fibers with significantly reduced energy input and very low static generation during debonding. The terms "debonded" or "debonding" should be considered to have the above meaning unless the context of usage of the words clearly indicate a different meaning; e.g., a chemical "debonding agent" as described earlier added to a pulp slurry to reduce strength of a sheet. The terms are synonymous with the words "defibered", "defibering", or "defiberizing". Unrefined pulps show essentially no reduction in water absorbency rate in the ultimate fluff. Other advantages of the product will also become apparent. The product comprises a relatively high basis weight wet formed cellulosic fiber sheet or web in which the fiber surfaces are coated with finely divided fillers in order to reduce fiber-to-fiber bond strength.

By wet forming is meant preparation of the sheet or web from a suspension in water by conventional papermaking techniques.

The pulp products of the present invention are clearly differentiated from products intended as letter, book, magazine, or similar papers. These are usually relatively highly refined to develop web strength and most have basis weights under about 100 g/m$^2$. Some specialty papers, such as cover stocks, may have basis weights that are significantly higher. Good strength is essential. Papers are normally sized to improve ink holdout and other printing properties. The products of the present invention are unsized and the strength properties such as tensile, burst, and tear strength, which are considered essential in papers, are generally much lower.

The basis weight of the products of the present invention may be as low as about 250 g/m$^2$ and are preferably at least about 550 g/m$^2$. The fiber will most usually be unrefined or only lightly refined although the invention is not so limited. Where a high surface area product is desired the fiber will normally be significantly refined. The filler is present in an amount ranging between about 1–30% based on the combined weight of filler and cellulose, more preferably between about 3–20%. The higher basis weight of the products, their lower strength, and the fact that they are unsized is such as to clearly distinguish them from ordinary papers which might contain similar amounts of fillers.

The cellulose pulp of the invention may be made using conventional kraft, sulfite, chemithermomechanical or other well known processes. The furnish can be from any of various cellulose containing raw materials. Most usually these will be deciduous hardwoods; coniferous species, usually termed softwoods; or mixtures of these materials. A preferred pulp is a bleached softwood kraft pulp that would normally be intended for ultimate use as absorbent fluff. While so-called "dissolving pulps" may be used these are not preferred because of their low yield and resultant much greater cost.

Among the mineral fillers that are suitable are clays, both kaolin and bentonite; calcium carbonate such as ground chalk, limestone, or marble or precipitated calcium carbonate; and synthetic mineral fillers such as alumino-silicates or precipitated silica. While titanium dioxide is normally used as a pigment for improving brightness it can also serve as a mineral filler. Talc (magnesium silicate) may be useful for some purposes. This is normally not preferred in the liquid storage portion of absorbent products such as diapers since it tends to decrease wicking rates and hydrophillcity. However, for some products such as oil absorbents, or where control of hydrophilicity is desired, this property can be advantageous. Certain organic fillers such as urea-formaldehyde or polystyrene microsphere types are also believed to be suitable. The term "fillers" should be construed sufficiently broadly to include those named above as well as other inorganic, organic, and synthetic inorganic filler materials in common papermaking use. Kaolin clays are the preferred fillers.

Fillers are present in the product in a range of about 1–30% of total product weight, preferably in the range of 3–20% by weight, and most preferably about 5–20% by weight.

The fillers are bonded to the fibers by the use of retention aids used in an amount of about 0.5–5 kg/t of fiber, typically about 1–3 kg/t, although this will depend somewhat on the particular retention aid being used. The retention aid should not be used in excess and should be added to the fiber prior to addition of filler so that it is bonded to the fiber with little or none remaining free in the pulp slurry prior to addition of the filler. This is done to promote bonding of the filler directly to the fiber and discourage flocculation of the filler.

While not the most preferred procedure, it is within the scope of the invention to use the opposite approach and first alter the negative charge on the filler particles by treating them in an aqueous suspension with a retention aid and then adding the cationic or less anionic treated particles to the untreated cellulose fibers. It is also possible to mix fibers and filler particles and then add a suitable retention aid. However, it is important that the retention aid used and the conditions of use should be such as to avoid any significant flocculation of the particles and ensure even deposition on the fibers.

It is an object of the invention to provide a sheeted fluff pulp that is readily debonded with reduced energy input.

It is another object to provide a sheeted fluff pulp that is readily debonded yet produces a fluff that retains an excellent water absorption rate.

It is a further object to provide a sheeted fluff pulp that is not subject to static electricity generation during the debonding process.

It is also an object to provide a readily debonded pulp product having an exceptionally high surface area.

It is yet another object to provide a process for making fluff pulps having the properties noted above.

It is still an object to provide a pulp product that is soft and absorbent that may be used directly as a component in personal care products.

These and many other objects will become readily apparent to those skilled in the art upon reading the following detailed description along with reference to the figures.

DETAILED DESCRIPTION OF THE PREFERRED EMBODIMENTS

Figure 1:
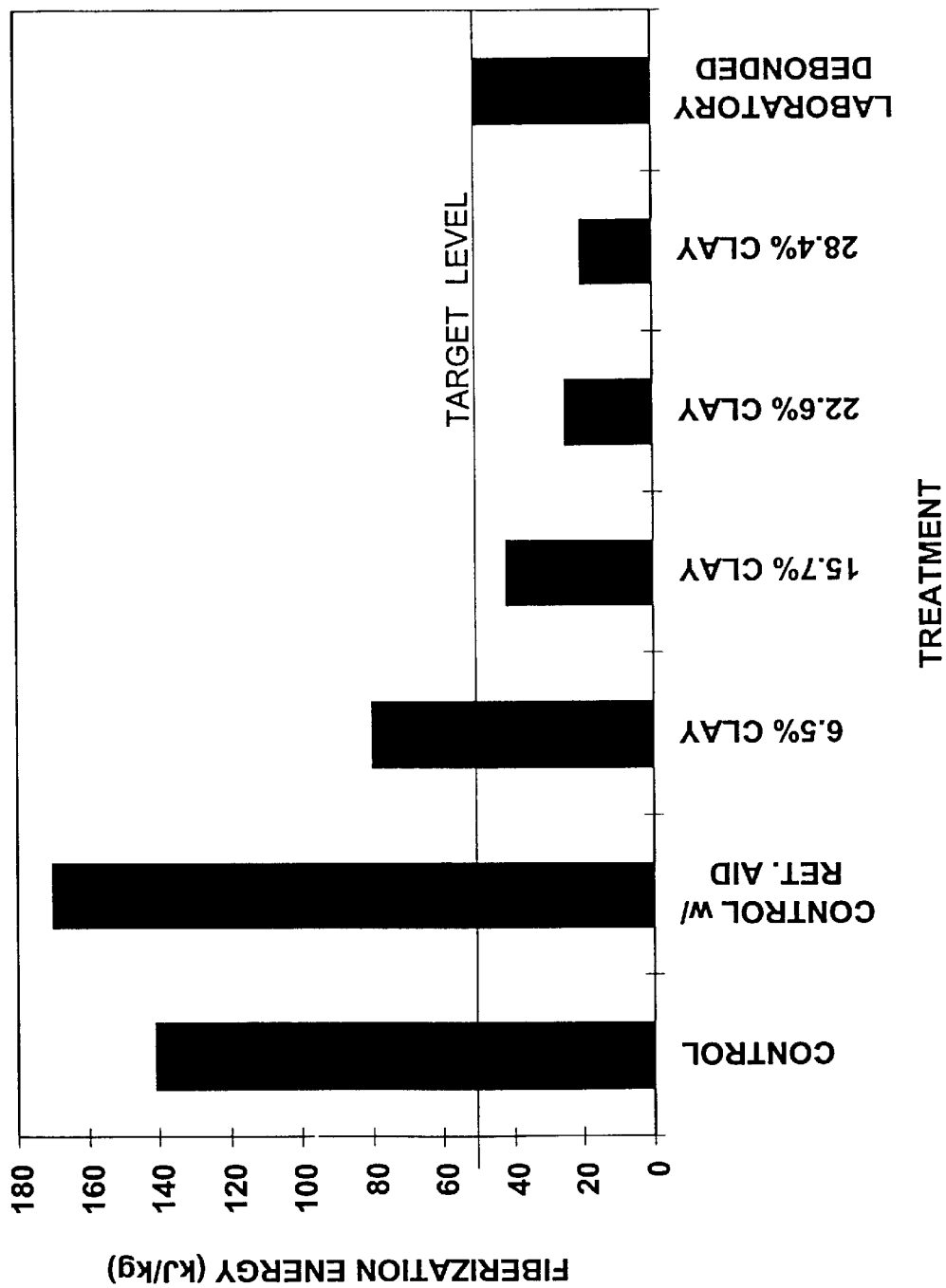
FIG. 1 is a bar graph showing fiberization energy of the various product samples.

The product of the invention can be produced by employing wholly conventional papermaking techniques as will be seen from the following example. Three test methods are generally used to evaluate fluff pulp quality. Fiberization energy requirement is determined using a laboratory scale hammermill instrumented to measure power necessary to fiberize a given weight of pulp. The mill used in the following tests was a Kamas Laboratory Mill, Model H01, manufactured by Kamas Indust, AB, Vellinge, Sweden. The breaker bar clearance of the mill was set at 4.0 mm, the screen size was 19 mm, and rotor speed was adjusted to 3024 rpm. Samples were conditioned at 50% R.H. for a minimum of 4 hours prior to testing. The samples were cut into strips 5.0 cm wide and as long as the sample would permit. Sufficient strips were cut to yield about 150 g of fiberized pulp. Basis weight of the samples was previously determined and the hammermill feed roller speed was adjusted to achieve a target feed rate of 2.80 g/sec.

Fiberization efficiency is determined by dry fractionation using a sonically agitated screen stack using Tyler Standard Screens of 5, 8, 12, 60, and 200 mesh having respective openings of 3.96 mm, 2.36 mm, 1.40 mm, 246 $\mu$m, and 74 $\mu$m. This is basically a determination of the percentages of knots, desired fiber, and fines. Material retained on the coarsest screen is considered to be knots and that through the 60 mesh screen is considered fines.

Water absorption rate was determined by using the automatic fluff absorption quality (FAQ) test described in detail by Martinis et al., Tappi Annual Meeting Preprint No. 7–3, pp 1–8, Chicago (1981). The fluff is first formed into an air formed pad within a cylinder 160 mm long and 56.4 mm in diameter having a 16 mesh screen at the bottom. Pad area is 25 cm$^2$. The tared cylinder is placed on a balance and pad weight adjusted to 4.0 g by carefully removing any excess fiber from the top with tweezers. The pad within the cylinder is then placed in the tester and a 150 g plunger lowered onto the fluff mat. Water is then introduced at the base of the pad. Absorption rate is calculated from the time required for water wicking from the bottom of the pad to contact the plunger; i.e., through the pad thickness. Dry bulk, wet bulk, and liquid holding capacity can also be readily determined

EXAMPLE 1

Samples were obtained of a never dried bleached southern pine kraft wood pulp from a southeastern U.S. pulp mill. The pulp when sheeted and dried at the mill is sold as Grade NB-416 by Weyerhaeuser Company, New Bern, N.C. This grade is produced as a market fluff pulp and was used as a control material in all of the examples that follow. Other materials used were a retention aid "7135" supplied by Nalco Chemical Company, Naperville, Ill. and a kaolin clay supplied as a 60% slurry designated SWW supplied by J. M. Huber, St. Louis, Mo. The retention aid is a medium molecular weight cationic polyamine in a solution with 50% active material. This was diluted with ten parts of water to one part 50% a solution before use and was used at a rate of 3 kg/t based on the combined oven dry weight of clay and fiber.

Hand sheets 305×305 mm were made using unrefined pulp at a targeted basis weight of 750 g/m² and density of 600 kg/m³. Clay retention was targeted at 5%, 10%, 20% and 30%. One batch of sheets was made without retention aid to see how much clay would be retained by physical entrapment in the sheets. Ash content of these sheets showed that virtually no clay was retained. The clay particles were so fine that the very open unrefined fiber matrix failed to capture them by filtration and virtually all of the clay passed out into the white water.

As was noted earlier, in most papers it is desirable to flocculate the mineral filler while leaving the fiber surface relatively uncoated. This enables maximum strength retendried between blotters then wet pressed at a pressure of 380 kPa. After drying at 105° C. and conditioning, sheets were tested for required debonding energy, fluff quality evaluation, absorption properties, and clay retention. Dried hand sheets were tested for ash content before and after fiberization. Comparison sheets were also made using 3 kg/t of commercially available debonder (Berocell 509, available from Eka Nobel) to simulate commercially available debonder treated fluff pulps using this approach. An additional control sample was made using only retention aid without any clay. Table 1 shows the sheet and resultant fluff properties obtained.

TABLE 1

Properties of Hand Sheets and Fluff with Clay Added

| Treatment | Control | Control + Retention Aid | Targeted Clay Level | | | | Lab. Debonder Treated |
|---|---|---|---|---|---|---|---|
| | | | 5% | 10% | 20% | 25% | |
| Sheet Properties | | | | | | | |
| Basis weight g/m² | 703 | 704 | 739 | 768 | 767 | 730 | 712 |
| Caliper, mm | 1.33 | 1.37 | 1.46 | 1.4 | 1.36 | 1.22 | 1.53 |
| Density, kg/m³ | 530 | 514 | 508 | 549 | 562 | 600 | 466 |
| Clay[1], % (sheet form) | 0.1[2] | — | 6.5 | 15.7 | 22.6 | 28.4 | — |
| Clay[1], % (after fiberization) | 0.1[2] | — | 6 | 14.2 | 20.6 | 26.6 | — |
| Fluff Properties | | | | | | | |
| Defibering Energy, kJ/kg | 143 | 170 | 79 | 42 | 25 | 18 | 50 |
| Total knots, % | 1 | 3 | NA | 1 | 1 | 1 | 1 |
| Absorption by FAQ Test | | | | | | | |
| Absorption time, sec | 3.1 | 3.1 | 2.6 | 2.3 | 2.2 | 2.1 | 5.3 |
| Absorption rate, mm/sec | 27.7 | 28.8 | 31.1 | 28.1 | 25.8 | 25.7 | 15 |

[1]Determined by dividing ash content by a factor of 0.86.
[2]Actual ash content.

tion from hydrogen bonds between fibers but the increased size of the mineral filler flocs is sufficient to allow them to be captured by the fiber web during sheet formation. For the present invention an opposite mechanism is desired. Formation of filler flocs is discouraged while maximum attachment to and coating of the fibers is the preferred mechanism. This is accomplished by first adding the retention aid to the fiber suspension and allowing a sufficient time for substantially all of it to bond to the fiber surface. Only then is the mineral filler added to the fiber slurry. The amount of retention aid used should not exceed that which will bond to available anionic sites on the fiber. Otherwise filler flocculation may occur. While this is not especially harmful to achieving the goal of improved debonding characteristics it does represent a waste of both retention aid and filler.

Based on the target basis weight the required amount of never dried pulp was weighed and retention aid at a 3 kg/t loading was added to the pulp slurry which was at 2–3% consistency. The mixture was stirred for about 20 minutes to permit maximum attachment of the retention aid to the fiber. The slurry was drained to remove any unbonded retention aid free in the suspension. However, later tests showed this step to be unnecessary. The desired amount of clay was then added to the drained pulp, water was also added to return the consistency to 2–3% and the slurry stirred an additional five minutes to permit the clay to bond to the fiber surfaces.

Hand sheets were formed at a pulp consistency, based on fiber plus retained clay, of 0.2%. The sheets were initially Several features of the clay coated product are readily apparent from reference to Table 1. The clay added is practically quantitatively substantive on the retention aid treated fiber and surprisingly little clay is lost during fiberization. Defiberization energy at all levels of clay usage is dramatically lower than that required for the control pulp and at usages of 10% or higher is significantly lower even than the debonder treated pulp. Of particular importance, water absorption rates of all the clay treated samples are not reduced relative to the control samples and are about 65% higher than the debonder treated material. Water absorption times are about 35% faster than the control pulp and over twice as fast as debonder treated pulp. The control sample with retention aid but no clay had closely similar properties to the untreated control pulp except in its slightly higher fiberization energy requirement. What is not shown in the table was the subjective observation that, in marked contrast to the control samples, the clay treated sheets showed little or no static generation on defibering.

The fiberization energy data from Table 1 are shown graphically in FIG. 1. It is noted that fiberization energy increases by 20% from addition of the retention aid alone. Apparently the retention aid by itself enhances fiber-fiber bonding. However, fiberization energy decreases below the control pulp even at the lowest level of clay addition and continues to drop as the clay content increases. At the 13.5% level of clay loading the fiberization energy is reduced to a level below that of the chemically debonded sheets with at an energy input only about 30% of that of the control. It is evident that the filler particles are highly effective at disrupting fiber-to-fiber bonding, even at low levels of addition.

Figure 2A:
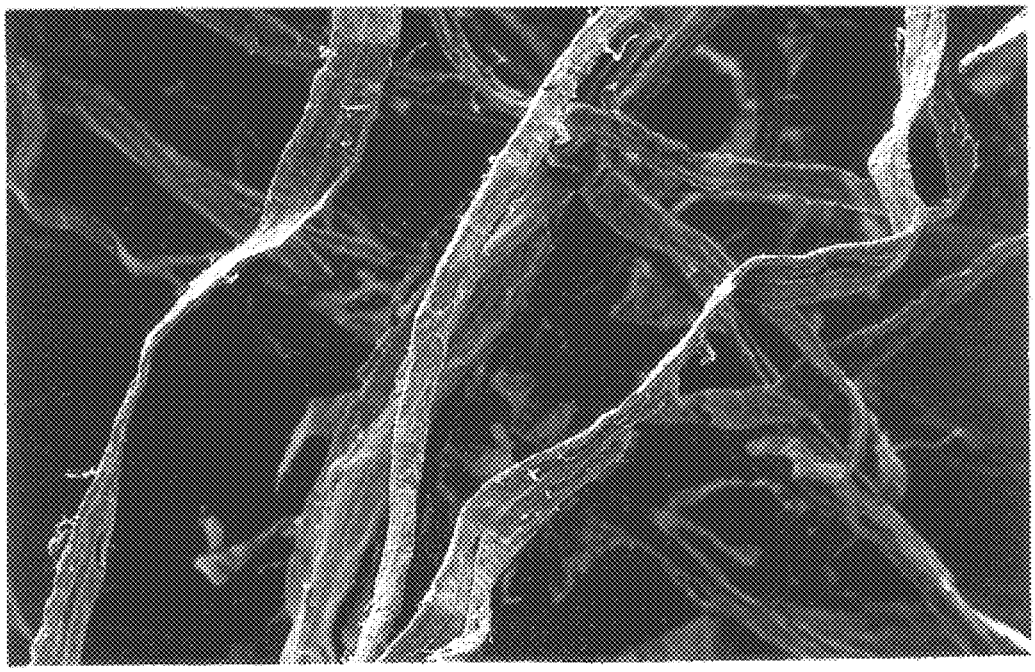
FIGS. 2A, 2B, 3A, and 3B are scanning electron micrograms of untreated fibers and treated fibers with 24.4% clay at respective magnifications of 150× and 8000×.
Figure 2B:
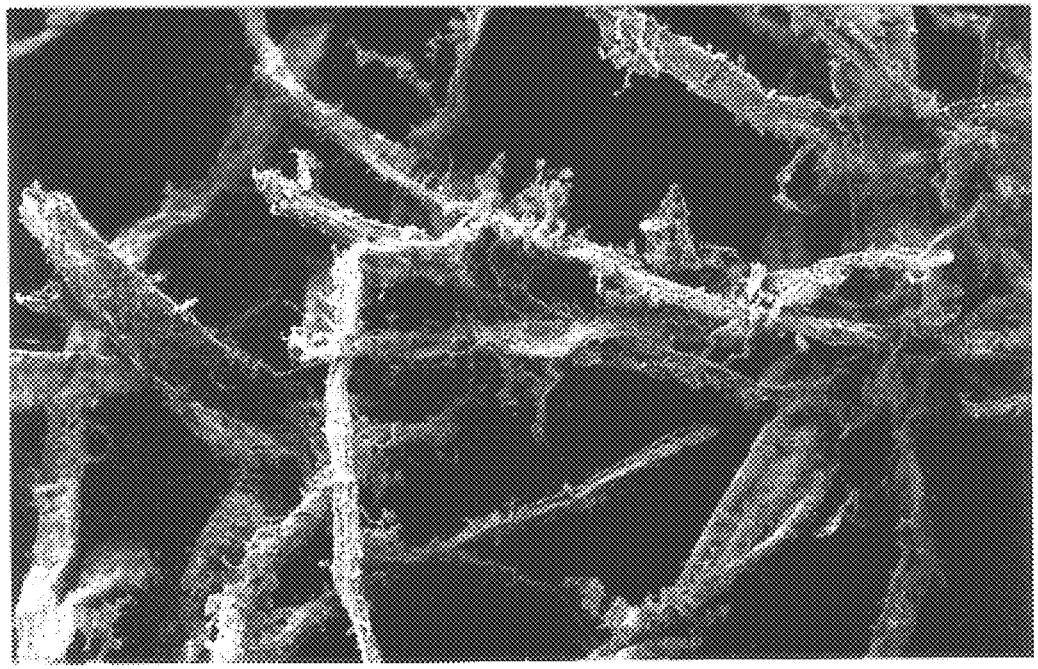
Figure 3A:
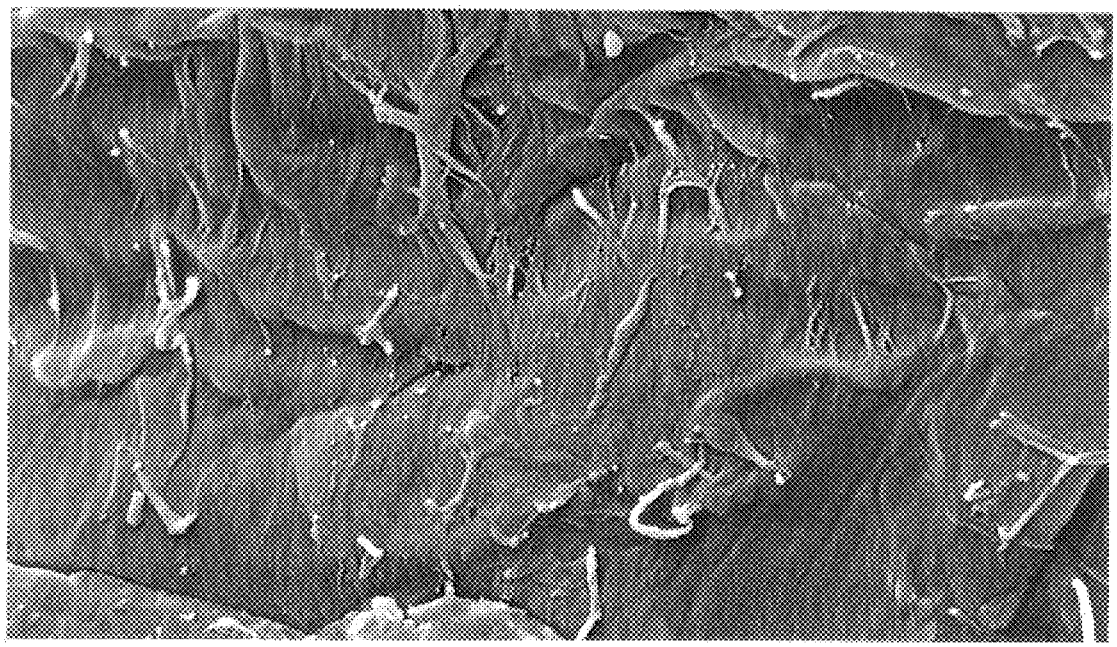
Figure 3B:
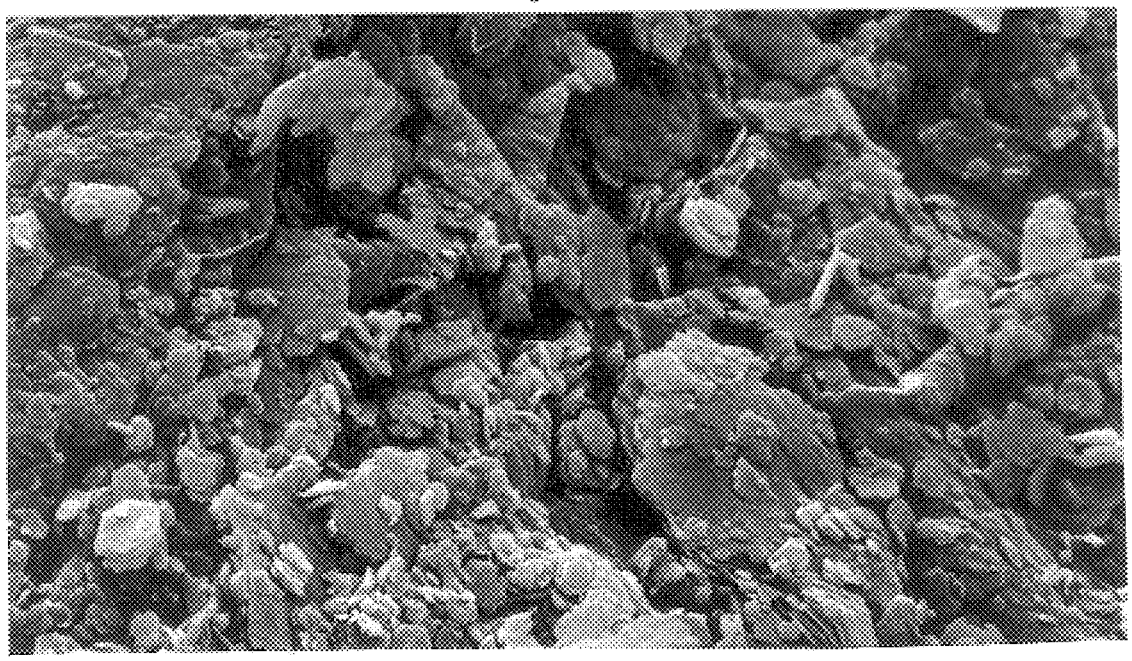

Scanning electron micrographs of the fibers were revealing. As seen in FIGS. 2A and 2B, at a relatively low magnification of 150× the untreated control fibers were seen to have a clean smooth surface while the treated fibers with 24.4% clay had a scaly rough surface. At the higher magnification of 8000×, shown in FIGS. 3A and 3B, the individual clay platelets on the treated fibers are easily observed. Surface coverage even with as low as 5% clay content (not shown in the micrographs) was surprisingly complete and uniform and this was even more the case at the higher loadings.

Figure 4:
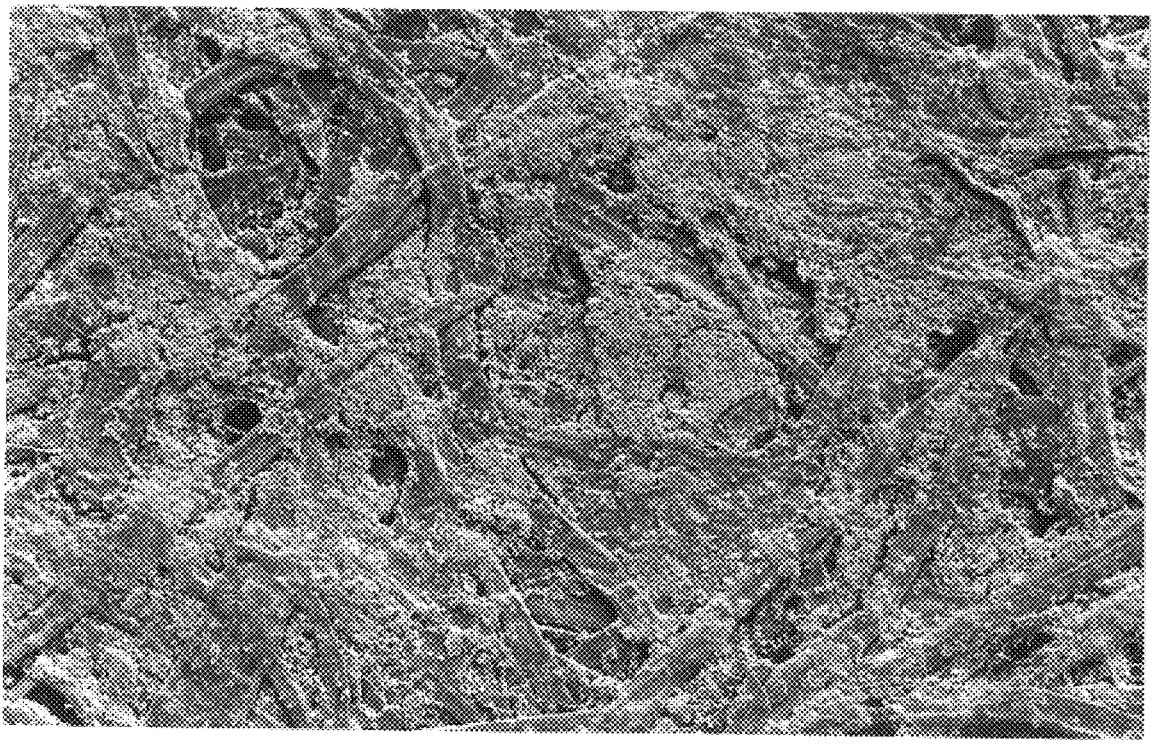
FIG. 4 is a scanning electron micrograph of a filled lithographic paper showing flocculated filler particles.

Even when the pulp was not refined, as in the present case, there is usually at least a minor amount of fibrillation that occurs during the pulping and bleaching process. In the scanning electron micrographs of FIG. 2A it is revealing to note that very few fibrils are seen on the surface of the uncoated fibers. However, significantly more fibrils are seen on the clay coated samples. As is apparent in FIG. 3A, these stood out much like the bristles of a brush and are, along with the body of the fiber, coated with clay particles to give a dendritic appearance similar to rime frost. Comparison of FIG. 2B with FIG. 4 clearly shows the marked difference between the fluff pulp of the present invention and a filled paper. The scanning electron micrograph at 200× of FIG. 4 is of the felt side of a lithographic paper with a calcium carbonate filler. In the product shown relatively little filler clings to the fibers but it is retained mostly as flocs in the interfiber interstices.

Figure 5:
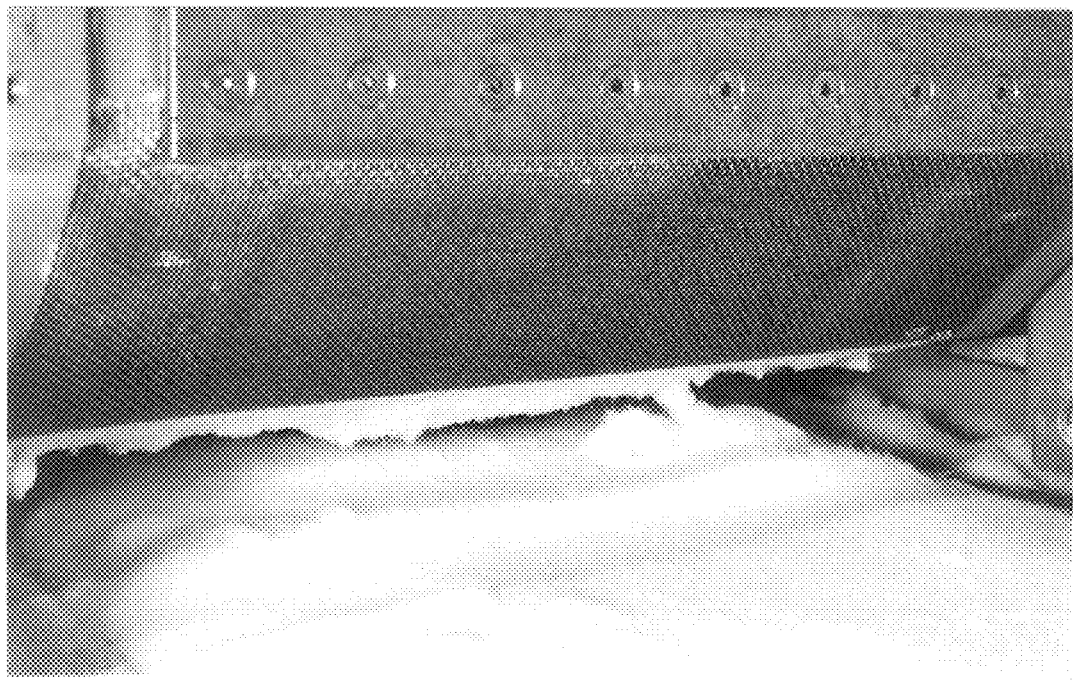
FIGS. 5 and 6 are photographs showing respectively the effects of static electricity generation on untreated pulp vs a product of the present invention.
Figure 6:
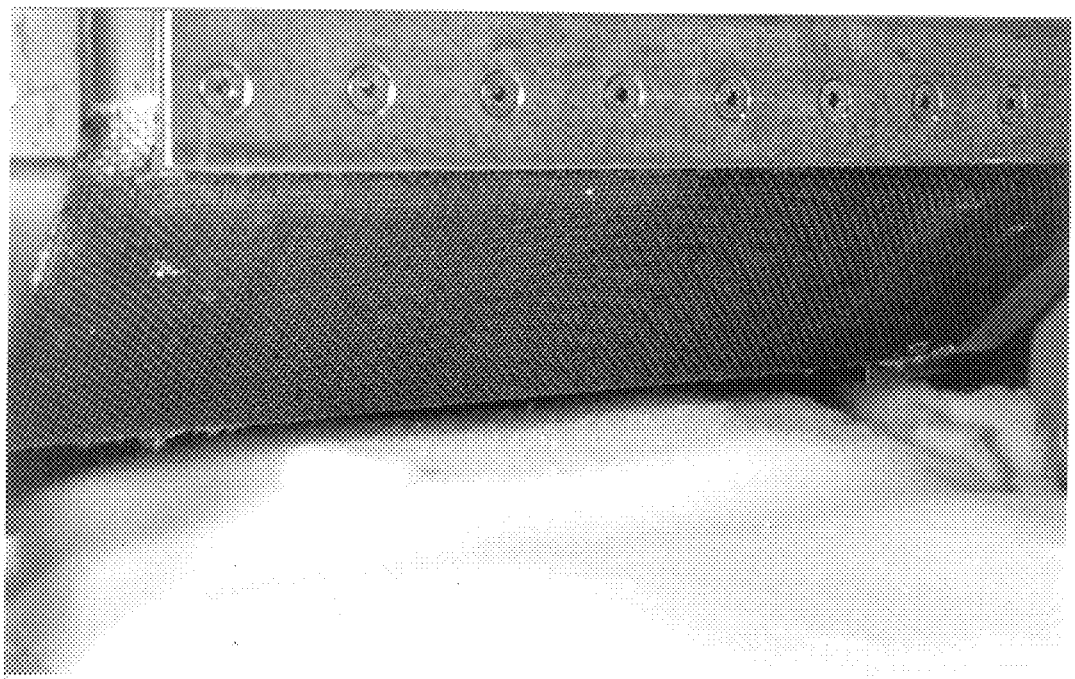
Figure 7:
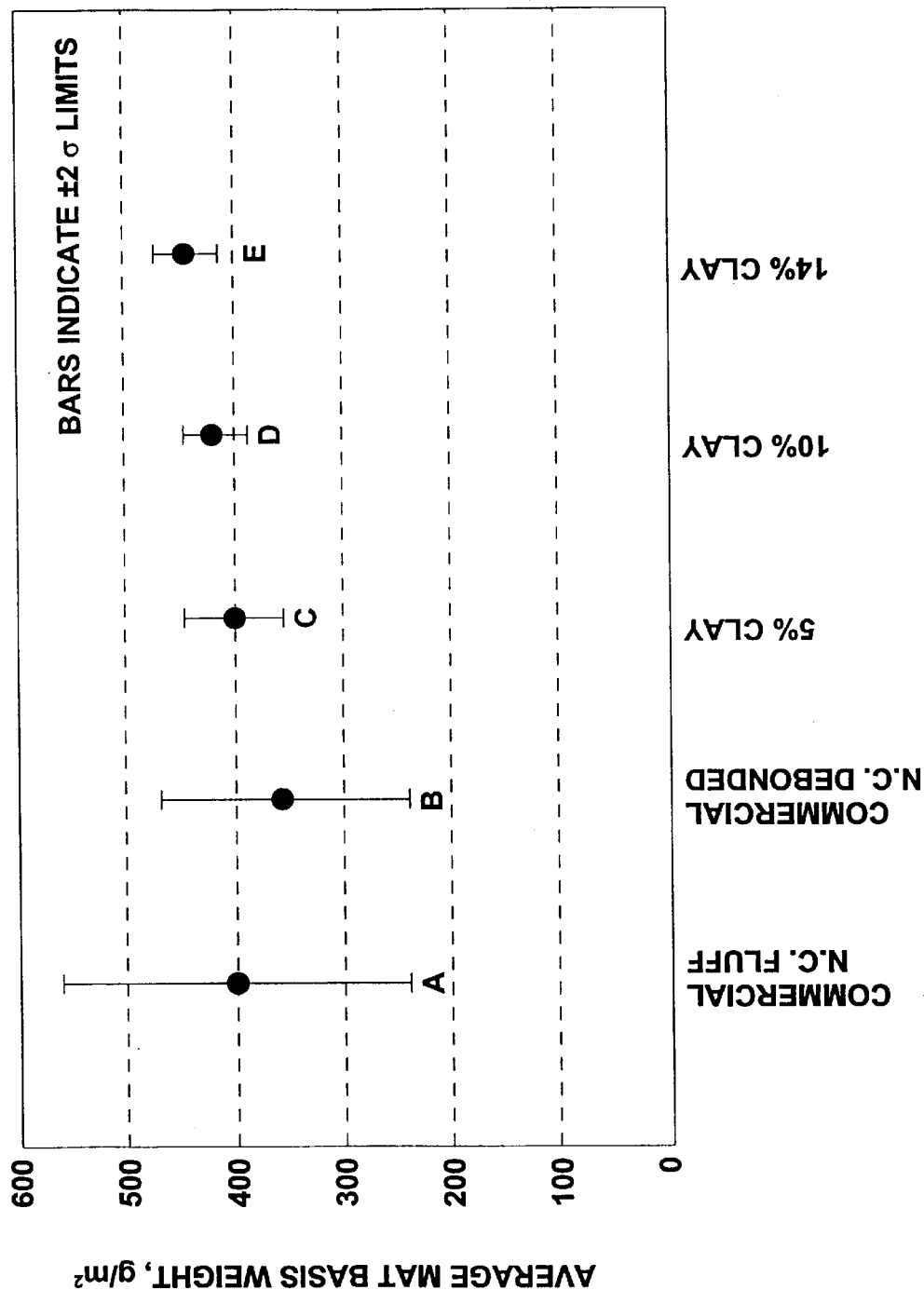
FIG. 7 is a graph showing variation in basis weight of air laid mats formed from conventional fibers and from those of the present invention.

Electrostatic phenomena were observed qualitatively during fiberization and mat formation. Electrostatic buildup was observed to be very significant for chemically debonded pulp in comparison with the untreated control while essentially no static buildup was observed in the clay treated material. This is clearly shown in the photographs of FIG. 5, using an untreated fluff pulp, and FIG. 6 where the pulp is a product of the present invention. The gobs of suspended fiber and poorer mat formation are clearly visible in FIG. 5. These fiber gobs eventually are rubbed off onto the mat and form lumpy areas or, by dragging against the mat, may form stripes which are under-weight zones. This is shown quantitatively in FIG. 7 where basis weight variation of continuously formed mats is shown. Two commercially available North Carolina kraft fluff pulps are used for comparison. One was untreated and the other was debonder treated. The clay treated pulp materials were from the large scale pilot trial to be described in Example 3. Vertical bars on the graph represent two standard deviations in mat weight. The superior uniformity of the clay treated pulps is immediately evident and is due to the reduced static generation during fluff production.

EXAMPLE 2

The samples described in Example 1 were all based on handsheets. These normally correlate well in most properties with machine run pulps. However, since the addition of clay to an essentially unrefined pulp is a radical departure from normal papermill practice, a run was made on a continuous Noble and Wood pilot scale paper machine having a 30 cm trim width. Materials and target basis weight and density on the pilot machine were identical to those used in Example 1. The identical never dried southern pine bleached kraft wood fiber was again used. The fiber was slurried in water at 2–3% consistency and retention aid at 3 kg/t usage was added with continuous stirring for about five minutes. The stock was drained to about 20% consistency, and water again added to bring consistency back to the 2–3% level. Clay was then added at levels sufficient to achieve about 5% and 10% loading levels. After mild agitation for about 5 minutes consistency was reduced to about 0.7% and the pulp slurry was then continuously sheeted. Results are seen in Table 2.

TABLE 2

Properties of Clay Treated Pulp from Pilot Scale Trial

| | Commercial Pulps | | Pilot Scale Pulps | | |
| --- | --- | --- | --- | --- | --- |
| Sample | Untreated Pulp | Debonder Treated | Control | 5% Clay | 10% Clay |
| Sheet Properties | | | | | |
| Basis Weight, g/m² | 780 | 700 | 474 | 456 | 584 |
| Density, kg/m³ | 605 | 515 | 445 | 524 | 469 |
| Chemical Properties | | | | | |
| Clay, % In sheet form[1] | — | — | — | 7 | 11.6 |
| Clay, % In fluff form[1] | — | — | — | 7 | 10.5 |
| Fluff Properties | | | | | |
| Defibering Energy, kJ/kg | 138 | 53 | 79 | 41 | 38 |
| Total knots, % | 11 | 1 | 3 | 0 | 0 |
| Absorption by FAQ Test | | | | | |
| Absorption time, sec | 2.8 | 5.8 | 2.8 | 2.4 | 2.2 |
| Absorption rate, mm/sec | 28.8 | 14.6 | 32 | 34.1 | 36 |

[1]Determined by dividing ash content by 0.86.

Due to mechanical limitations, the targeted conditions of basis weight and density could not be achieved on the pilot machine. The values obtained for these two properties were significantly lower than those desired. However, it is again evident that clay addition was substantive and that defiberization properties were similar to those of the hand sheets. Even the addition of a nominal 5% clay reduced defiberization energy to almost half that of the pilot sheeted control.

EXAMPLE 3

Since it was not possible to reach the desired higher basis weight due to machine limitations using the Noble and Wood pilot scale paper machine, a similar run was made on a larger 91 cm (36 in) trim width pilot machine at Herty Foundation, Savannah, Ga. Al runs were made using an undried pulp similar to that used in Examples 1 and 2.

TABLE 3

Properties of Clay Treated Pulp from Larger Pilot Scale Trial

| | | Targeted Clay Level | |
|---|---|---|---|
| Treatment | Control | 5% | 10% |
| Sheet Properties | | | |
| Basis weight g/m$^2$ | 724 | 687 | 766 |
| Caliper, mm | 1.15 | 1.07 | 1.28 |
| Density, kg/m$^3$ | 630 | 640 | 601 |
| Clay$^{(1)}$, % (sheet form) | — | 5.4 | 14.2 |
| Clay$^{(1)}$, % (after fiberization) | — | 5.4 | 12.9 |
| Fluff Properties | | | |
| Defibering Energy, kJ/kg | 127 | 72 | 26 |
| Total knots, % | 30 | 1 | 1 |
| Absorption by FAQ Test | | | |
| Absorption time, sec | 2.4 | 2.2 | 2.1 |
| Absorption rate, mm/sec | 30.1 | 36.6 | 32.2 |

$^{(1)}$Determined by dividing ash content by 0.86.

It is evident that basis weight has little effect on the defibering and absorption rate properties of the pulps since results are similar to those seen in Table 2.

EXAMPLE 4

Figure 8:
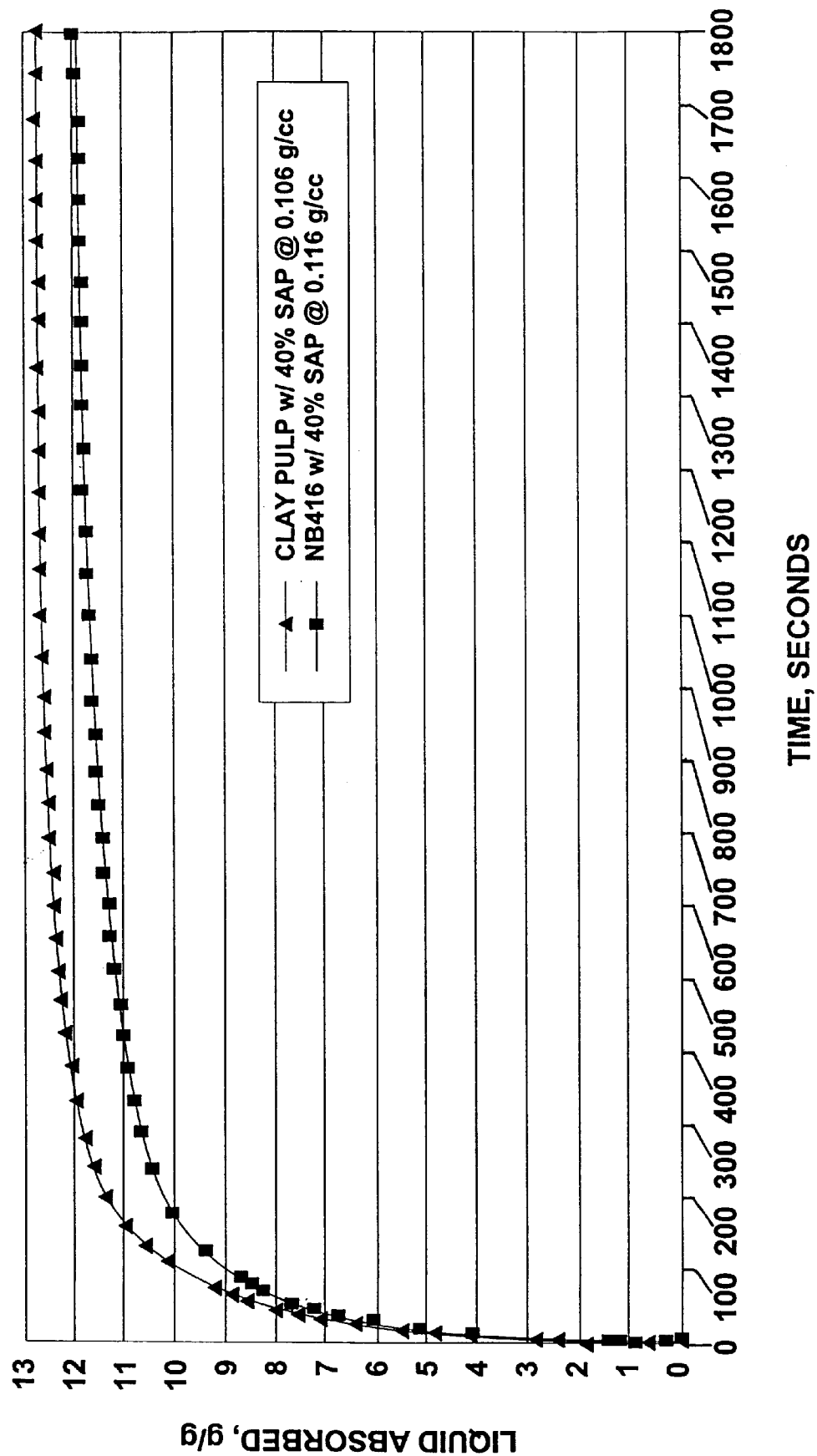
FIG. 8 is a graph showing liquid absorbed vs time for a treated and untreated fiber with added superabsorbent polymer.

Most personal hygienic absorbent products are now predominantly made using superabsorbent polymers (SAP) in conjunction with the cellulosic fluff. In some cases the polymer particles are physically attached to the fibers by various mechanisms, for example as seen in Hansen et al. U.S. Pat. No. 5,308,896. More commonly the fiber and SAP particles are simply mixed in an air stream during pad formation. Pads of the latter type were made using the pulp sheets with clay at the 10% level made in the Noble and Wood pilot trials described in Example 2. The sheets were fiberized and mixed with 40% based on ultimate product weight of a SAP, IM 3900 available from Hoechst Celanese Corp., Charlotte, N.C., during formation of air laid pads. A similar set of samples was made using a commercially available southern pine bleached kraft fluff pulp The never dried fiber used in all of the experiments was obtained from the furnish used for manufacture of this commercial pulp. The pads were compressed to similar densities, about 0.11 g/cm$^3$, under identical applied loads and submitted for a gravimetric absorption test. In this absorption test the pads are held under an applied load of 3.4 kPa and are wet from the bottom by a synthetic urine composition. Weight increase from liquid uptake is continuously measured by an electronic balance and plotted as grams of liquid absorbed per gram of dry pulp/SAP composite as a function of time. FIG. 8 shows a plot of the clay treated pulp vs the commercial fluff pulp. Fluff from the treated pulp has an equilibrium capacity about 7% higher than its untreated equivalent. The results show an enhanced absorbency in compressed structures made in conjunction with superabsorbent polymers.

The clay treated fluffed pulp also was observed to exhibit greater softness and bulk after dry compaction under the same load compared to control pulp. This was observed both in the presence and absence of SAP.

EXAMPLE 5

As will be seen in this example, the present invention is not limited to kaolin clay as a filler material. Using the never dried fiber and procedures of Example 1, additional handsheet samples were made in which the kaolin clay was replaced with precipitated calcium carbonate, ground calcium carbonate, bentonite clay, and talc. The latter product was used to prepare a hydrophobic material. The furnish consisted of 65 g oven dry weight of the fiber and 14 g, solids basis, of the filler (17.7% filler). Materials and sources are as follows: precipitated calcium carbonate (PCC)—Specialty Minerals. Longview, Wash.; ground calcium carbonate (GCC)— Microna S-93, Columbia River Carbonate Company, Woodland, Wash.; bentonite clay—Hydrocol HSUF, Allied Colloids, Suffolk, Va.; and talc- XP961, Luzenac America, Englewood, Colo. Filler content of the sheets (by ashing), absorption rate, and debonding energy are seen in the following table:

TABLE 4

Products With Fillers Other Than Kaolin Clay

| Filler Material | Filler Retained, %$^{(1)}$ | Absorption Rate, mm/sec | Fiberization Energy, kJ//kg |
|---|---|---|---|
| Precip. CaCO$_3$ | 9.9 | 31.6 | 76 |
| Ground CaCO$_3$ | 7.4 | 34.2 | 87.9 |
| Bentonite clay | 6.4 | 30.5 | 70.8 |
| Talc | 17.6 | 0.3 | 92.4 |

$^{(1)}$Determined from ash content and corrected for known weight loss of filler during ashing.

It can be seen that despite the lower retention of mineral filler than was achieved with kaolin clay, absorption rate was equivalent and fiberization energy essentially halved from the control sample in Example 1.

EXAMPLE 6

Eriksson et al., in U.S. Pat. No. 5,492,759, describe a method of making an enhanced surface area cellulose fiber by depositing a silica coating on the fibers. The inventors found that liquid absorption rate was related to surface area. The techniques of the present invention can also be used to make an enhanced surface area fiber but using a process much simpler and more practical for typical paper mills than those of Eriksson et al.

While most fluff pulps are essentially unrefined or only lightly brushed in a refiner, the technology of the present invention can be applied to refined pulps to produce fibers of very high surface area in the dry state. The filler particles prevent collapse of the cellulose fibrils upon drying. Approximately 2 tons of never dried pulp similar to that of the previous examples were used in a pilot scale trial made on the 91 cm (36 in) trim width fourdrinier machine at Herty Foundation, Savannah, Ga. The pulp was refined to 230 mL CSF. A filler retention aid (Nalco 7607, Nalco Chemical Company, Naperville Ill.) was added at a rate of 3 kg/t. After a short reaction time 30% kaolin clay was added (based on dry pulp). A sheeted product was produced at a basis weight of 750 g/m$^2$ and 6% moisture content. Sheet density was 700 kg/m$^3$, slightly higher than target value. Approximately 750 kg of clay treated sheet was produced. Results of tests on the product are found in the following table.

TABLE 5

Results of Large Scale Pilot Run of Refined Pulp

| Sample | Mill Produced Unrefined Control | Refined Clay Treated |
|---|---|---|
| Clay content, %[1] | 0 | ca. 25 |
| Defibering energy, kJ/kg | 131 | 56 |
| FAQ Absorption Rate, mm/sec | 28.8 | 15.5 |
| Surface Area, m²/g [2], defibered | <1 | 7.6 |

[1] Determined from dividing ash content by 0.86.
[2] B.E.T. Nitrogen absorption method Defibering energy of the clay treated pulp was significantly reduced compared with the commercially produced unrefined pulp used as a control sample. Surface area of the treated material was equal or superior to the best obtained by Eriksson et al. Surface area of the treated sheeted pulp before defibering was measured as 7.2 m/g². It was noted subjectively that opacity of the material was exceptionally high. The lower absorption rate of the clay treated material was expected for a refined pulp.

Even lighter refining than that used for the above material can contribute substantially to increased surface area. Improvements are seen at freeness values as high as 550 CSF although the most significant increase in surface area is obtained at freenesses of about 350 CSF or lower. While the absorption rate of the increased surface area refined products may be lower than unrefined pulps, the driving force for absorption is increased. This can be considered as analogous to a suction force tending to absorb and distribute a liquid with which the product is in contact. The greater driving force can be used to move liquid further, hold liquid more tightly and, in combination with other materials, move liquid more rapidly.

It may be advantageous to make blends of the high surface material just described with other fibers. These other fibers can be cellulosic, chemically modified cellulose, or noncellulosic in composition. As one example, a fiber having greater absorbency rates or higher bulk might be blended with the high surface area material to take advantage of the higher suction capability of the latter material. For example, this added fiber could be a conventional untreated cellulose fiber or one of the unrefined treated fibers of the earlier examples.

Blends with noncellulosic fibers can frequently be used to advantage. Exemplary of these noncellulosic fibers are synthetic polymer materials such as polyolefins, nylons, and polyesters.

The mixtures can have a ratio of 10–90% added fiber to 90–10% high surface area fiber. A particularly advantageous additive fiber would be a crosslinked cellulose fiber. Most typically the blend would have about 25% of the high surface area material and 75% of the crosslinked fiber. An exemplary crosslinked fiber might be one available from Weyerhaeuser Company, Tacoma, Wash. as High Bulk Additive or HBA™ fiber. The blends can be made at any time, either before or after addition of the retention aid and filler particles. Most typically, the refined fiber would first be treated with the filler, as in the present example, and then the added fiber would be added and thoroughly blended.

While it is anticipated that in most cases a blended product would be prepared in sheeted form, it should be considered to be within the scope of the invention if the product was prepared as bulk individual fibers; e.g., by flash drying or other known means.

Where the other fibers in admixture with the high surface area fibers are cellulosic, they would normally be refined only to a very high freeness value; e.g. 550 CSF or higher, or not refined at all.

EXAMPLE 7

Liquid holding capacity may be measured by the FAQ test noted earlier. Another procedure that is an indicator of actual performance in a diaper or similar article is the inclined wicking capacity test. A sample having dimensions of 7×30 cm is cut from an air laid fluff pad. This is placed on an acrylic plate on a stand inclined at a 30° angle. Pads nay be pressed to a predetermined density prior to commencing the test. The stand is on an electronic balance so that weight can be constantly recorded as a function of time. The end of the pad is then slid into a constant height water reservoir and weight gain over time is recorded. Tests are run in triplicate and results averaged.

Figure 9:
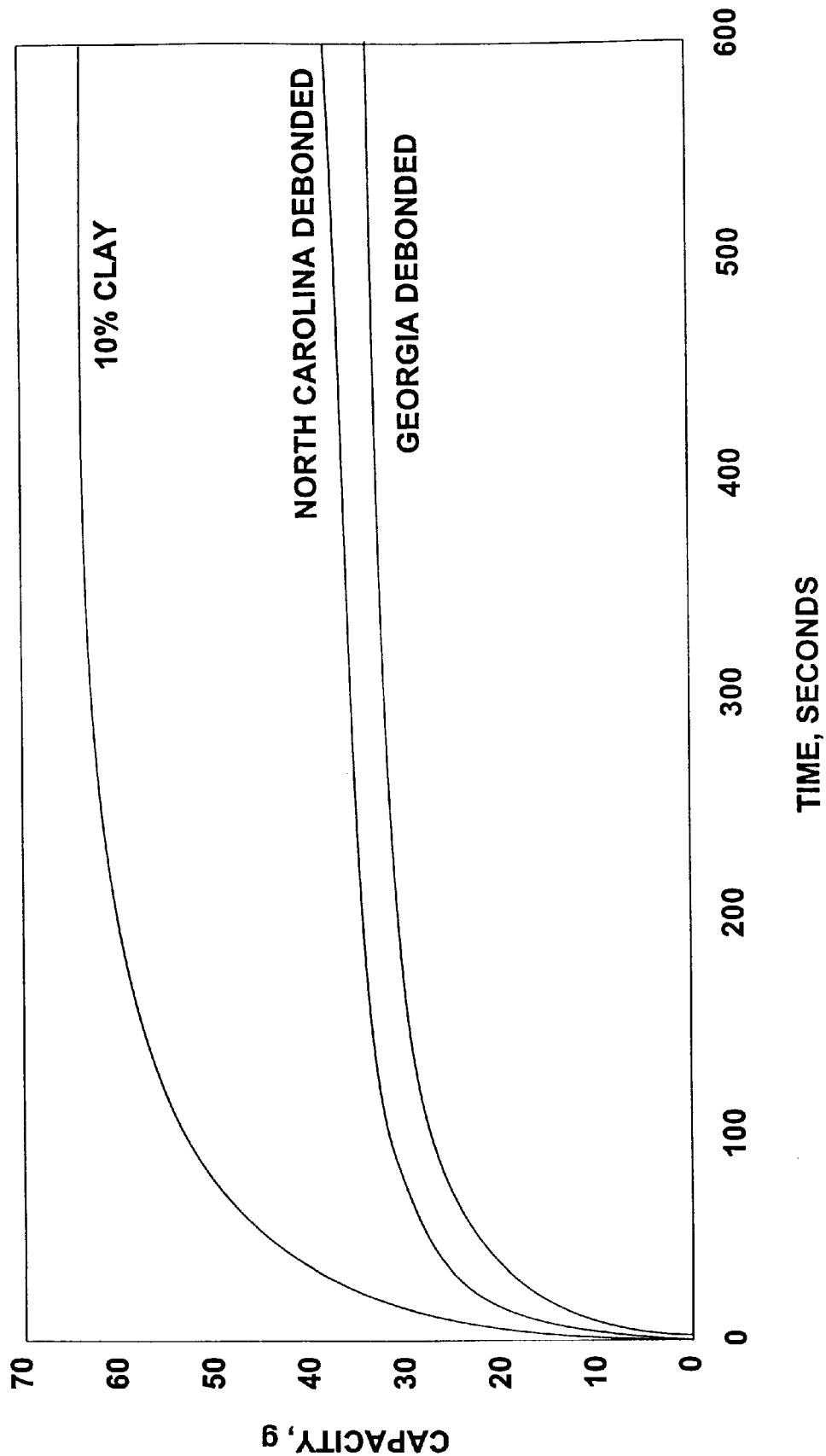
FIG. 9 is a graph showing liquid holding capacity vs absorption time for fluff pads formed from two commercial pulps and one product of the present invention using an inclined wicking test.

FIG. 9 shows results of tests on a 10% clay treated pulp, a compared with two commercially available debonder treated pulps. The very significantly increased liquid holding capacity of the clay treated sample is immediately evident.

EXAMPLE 8

Swedish Patent No. 462,918 describes the use of finely ground alpha cellulose as a fluff pulp additive for reducing debonding energy without the need for chemical additives. When sheeted, the alpha cellulose particles are said to prevent surface contact between the fibers and reduce natural hydrogen bonding forces. The alpha cellulose particles (alpha content of 92.5%) had been ground by undisclosed means to a particle size falling between about 0.001–0.1 mm. A usage of 10 kg/t (1%) was noted without any other chemicals being added. Sheets having a basis weight of about 800 g/m² were wet formed and dried. The sheets were defibered in an undescribed test apparatus and found to have a defibering energy of 150 kJ/kg compared with 400 kJ/kg for the untreated pulp. Absorption capacity was also slightly increased.

In an effort to duplicate the Swedish work the never dried control pulp used in the previous examples was treated with 1% and 4% of Avicel®Type-PH101 microcrystailine cellulose from FMC Corp., Newark, Del. This has an average particle size of about 50 μm which falls in the middle of the Swedish particle size distribution. Since no better description of the ground cellulose was given in the Swedish patent this material was chosen as its probable equivalent. Handsheets having a similar basis weight to the Swedish material were made.

In contrast to the Swedish results, no improvement in defibering energy was observed, as is seen in the following table. The experiment was repeated using a retention aid (Nalco 7607 at 1.5 kg/t) with results being similar to those without the retention aid. There was an increase noted in liquid holding capacity of the treated samples but no differences were seen in FAQ absorption rate.

It was subjectively observed that static generation during defibering and during formation for the FAQ test was high, about the same as the control sample.

TABLE 5

Use of Fine Cellulose Particles as Potential Debonding Aid

| | Control | 1% Fine Cellulose | 4% Fine Cellulose | 1% Fine with Ret. Aid | 4% Fine with Ret. Aid |
|---|---|---|---|---|---|
| Basis weight, g/m$^2$ | 785 | 778 | 772 | 768 | 768 |
| Density, kg/m$^3$ | 521 | 494 | 511 | 473 | 512 |
| Defibering energy, kJ/kg | 136 | 144 | 130 | 148 | 141 |
| Capacity, g H$_2$O/g | 8.5 | 11.5 | 11.4 | 11.6 | 11.4 |
| FAQ Absorption rate, mm/sec | 31.5 | 30.8 | 31.3 | 29.8 | 31.7 |

In general, all the products of the present invention will have a Kamas defiberization energy of less than about 90 kJ/kg. With the exception of the refined high surface area pulps, they will have a minimum FAQ wicking rate of at least about 25 mm/sec.

EXAMPLE 9

The high surface area product of Example 6 is blended before sheeting with a crosslinked cellulose fiber in a ratio of 25% of the clay treated fiber and 75% chemically crosslinked cellulose fiber by weight. The crosslinked cellulose fiber is supplied as HBA™ by Weyerhaeuser Company, Tacoma Wash. The mixed product is then sheeted and dried in normal fashion. After defibering in a hammermill an air laid web having a basis weight of 100 g/m$^2$ is made from the product. This web is strengthened by addition of a bonding material. In the present case 15% by weight of an ethylene vinyl acetate latex is sprayed onto both sides of the product after the web is formed. The bonded web is then dried and the latex cured. The product is beneficial as an aquisition/distribution layer in sanitary napkins or diapers As such it accepts an initial flood of fluid and distributes it into a storage zone. Alternatively, the product is useful as wipes.

As an alternative construction, the latex binder is replaced with a thermobondable fiber at the time the web is formed. A product of this type is prepared by uniform inclusion of 16% by weight Celbond fiber supplied by Hoechst Celanese Corp., Charlotte, N.C. Celbond is believed to be a bicomponent fiber having a polyester core and polyethylene sheath. The formed product is passed over a zone where heated air at about 130° C. is passed through it to create a strong bond.

EXAMPLE 10

Figure 10:
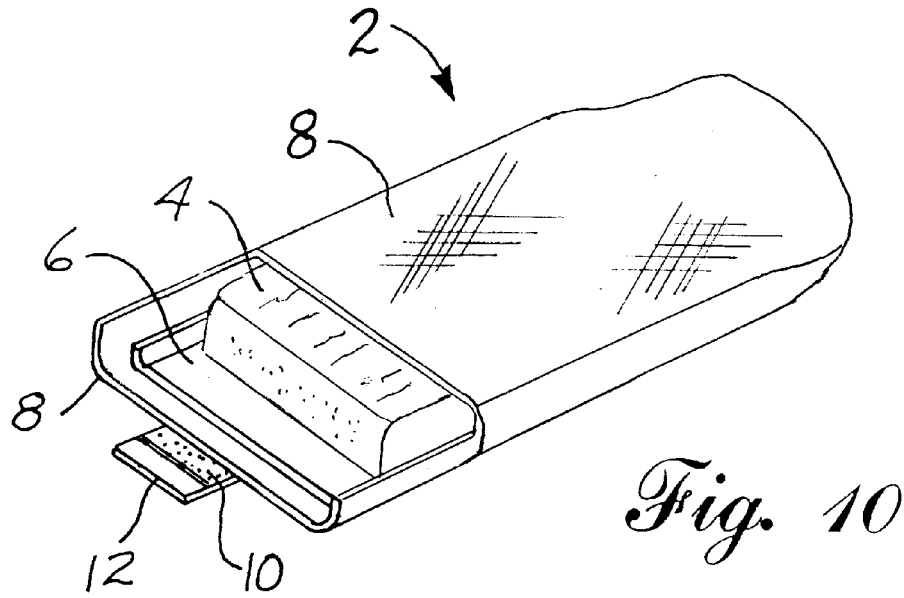
FIG. 10 shows a sanitary napkin for menstrual protection made using a product of the present invention.

Fiber made from defibered sheets similar to the product described in Example 4 is formed into a web and used to prepare sanitary napkins. The fiber used contains 10% kaolin clay. To this was added 15% by weight of the superabsorbent polymer to give an 85:15 mixture of treated fiber to SAP. As seen in FIG. 10, a sanitary napkin 2 was formed using as an absorbent core portion 4 an air laid web of the fiber/SAP mixture with a basis weight of 215 g/m$^2$ pressed to a thickness of 1.56 mm and density of about 0.14 g/cm$^3$. This fiber web is backed with a liquid impermeable thin sheet of polyethylene film 6 and enclosed within a moisture permeable nonwoven wrapper 8. A pressure sensitive adhesive 10 is formed on the lower side of wrapper and protected by a removable peel strip 12. Tests show the product to have excellent fluid absorbency.

In another construction, the sheeted product can be used directly, without defiberization, either as the sole absorbent component or as one component in a multiple layer absorbent core portion. Depending somewhat on the basis weight, density, and other properties of the sheet, it may or may not be desirable to further soften or tenderize it. This may be done by any of the well known methods; e.g., by needling or embossing.

EXAMPLE 11

Figure 11:
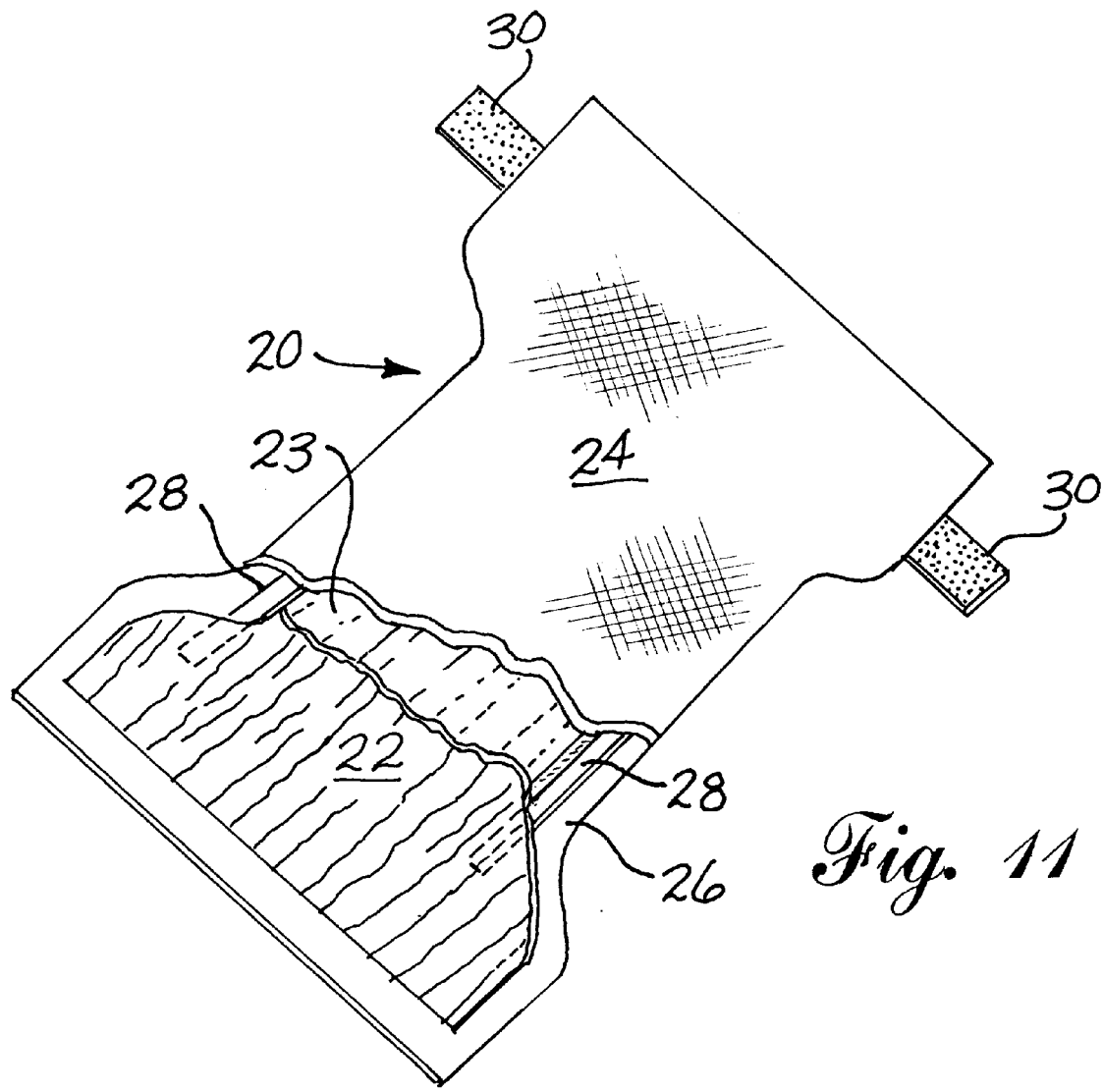
FIG. 11 similarly shows a baby diaper using one of the products of the invention.

In similar fashion to the product of Example 10, as seen in FIG. 11 a baby diaper 20 is made using a major core portion having 20 parts by weight of fluff and 10 parts of the superabsorbent polymer. The treated fiber from which the fluff is formed is similar to that of the previous example but contains only 5% by weight kaolin clay. The SAP containing fluff is air laid into a pad 22 having a basis weight of about 500 g/m$^2$. This fluff layer is used as the liquid storage portion of the diaper. This is overlaid by a lighter aquisition/distribution layer 23 having a basis weight of about 200 g/m$^2$ composed of the high surface area fibers prepared from the product of Example 6. Alternatively, layer 23 may be formed from a blend of high surface area fibers and crosslinked fibers such as Weyerhaeuser HBA fiber as was shown in Example 9. In turn, this is covered by a skin contacting, liquid permeable nonwoven web 24 and liquid impermeable polyethylene film backing 26. Elastic strips 28 along the edges assist in preventing leakage when the diaper is in use. Adhesive strips 30 are used to secure the diaper to the infant. The product has excellent absorbency of a synthetic urine composition Optionally, high surface area fibers could be used as a component of the core.

The products of the present invention present many advantages over similar products previously available. It will be understood by those skilled in the art that many variations will be possible in the products and method of their production that have not been suggested in the examples. Thus, it is the intention of the inventors that these variations should be included within the scope and spirit of the invention if they are encompassed within the following claims.

We claim:

1. A readily defibered wet laid cellulose product having a basis weight of at least about 250 g/m$^2$ in which interfiber bonds are minimized by an effective amount of fine mineral filler particles attached to said fiber surfaces before wet forming the product, the mineral filler particles being selected from the group consisting of clays, calcium carbonate, titanimn dioxide, talc, and mixtures thereof, the product having a Kamas fiberization energy less than about 140 kJ/kg.

2. The cellulose pulp product of claim 1 in which the basis weight is at least about 550 g/m$^2$.

3. The cellulose pulp product of claim 1 in which the mineral filler particles are kaolin clay.

4. The cellulose pulp product of claim 1 in which the mineral filler particles are present in an amount of about 1–30% based on the combined weight of particles and cellulose.

5. The cellulose product of claim 1 in which the mineral filler particles are present in an amount of about 3–20% based on the combined weight of particles and cellulose.

6. The cellulose pulp product of claim 1 in which the mineral filler particles are bonded to the cellulose fibers by a filler retention aid.

7. The cellulose pulp product of claim 1 in which the Kamas fiberization energy of the product is less than about 90 kJ/kg.

8. The cellulose pulp product of claim 1 which in fluffed form has a water wicking rate by a standard FAQ test greater than about 25 mm/sec.

9. The cellulose pulp product of claim 1 in which the fibers are essentially unrefined.

10. The cellulose pulp product of claim 1 in which the fibers are refined to a Canadian Standard Freeness less than about 350.

11. The cellulose pulp products of claims 9 or 10 in admixture with 10–90% by weight of other fibers selected from the group consisting of cellulosic, chemically modified cellulose, and noncellulosic fibers.

12. The cellulose pulp product of claim 11 in which the other fiber is a crosslinked cellulose fiber.

13. A readily defibered wet laid cellulose fluff pulp product having a basis weight of at least about 250 g/m$^2$ and characterized by low static generation upon subsequent defibering in which interfiber hydrogen bonds between cellulose fibers are substantially interrupted by an effective amount of fine mineral filler particles attached to said fiber surfaces before wet forming the product, the mineral filler particles being selected from the group consisting of clays, calcium carbonate, titanium dioxide, talc, and mixtures thereof, the product having a Kamas fiberization energy less than about 140 kJ/kg.

14. The cellulose pulp product of claim 13 in which the basis weight is in excess of about 550 g/m$^2$.

15. The cellulose pulp product of claim 13 in which the mineral filler particles are kaolin clay.

16. The cellulose pulp product of claim 13 in which the mineral filler particles are present in an amount of about 1–30% based on the combined weight of particles and cellulose.

17. The cellulose product of claim 16 in which the mineral filler particles are present in an amount of about 5–20% based on the combined weight of particles and cellulose.

18. The cellulose pulp product of claim 13 in which the mineral filler particles are bonded to the cellulose fibers by a filler retention aid.

19. The cellulose pulp product of claim 13 which has a fiberization energy less than about 90 kJ/kg.

20. The cellulose pulp product of claim 13 which in fluffed form has a water wicking rate by a standard FAQ test greater than about 25 mm/sec.

21. The cellulose pulp product of claim 13 in which the fibers are essentially unrefined.

22. The cellulose pulp product of claim 13 in which the fibers are refined to a Canadian Standard Freeness less than about 350.

23. The cellulose pulp products of claims 21 or 22 in admixture with 10–90% by weight of other fibers selected from the group consisting of cellulosic, chemically modified cellulose, and noncellulosic fibers.

24. The cellulose pulp product of claim 23 in which the other fiber is a crosslinked cellulose fiber.

25. A refined cellulose pulp product comprising cellulose fibers in admixture with 10–90% of fibers selected from the group consisting of other cellulose fibers, chemically modified cellulose fibers, and noncellulosic fibers in which interfiber hydrogen bonds are minimized by an effective amount of fine mineral filler particles attached to said fiber surfaces, the mineral filler particles being being selected form the group consisting of clays, calcium carbonate, titanium dioxide, talc, and mixtures thereof, the product having a Kamas fiberization energy less than about 140 kJ/kg.

26. The cellulose pulp product of claim 25 in which the cellulose pulp is refined to a Canadian Standard Freeness less than about 350 prior to attaching the noncellulosic particles.

27. The cellulose pulp product of claim 25 in which the other fiber in admixture is a crosslinked cellulose fiber.

28. A disposable absorbent product having an absorbent core portion comprising a readily debonded cellulose product as described in claim 1.

29. The disposable absorbent product of claim 28 comprising an absorbent core portion formed of fluff made by defiberizing and air laying into pad form the product of claim 1.

30. The disposable absorbent product of claim 28 comprising an absorbent core portion of which at least a portion is formed from the product of claim 1 in sheeted form.

31. A disposable absorbent product having an absorbent core portion comprising a readily debonded cellulose product as described in claim 10.

32. The disposable absorbent product of claim 31 comprising an absorbent core portion formed of fluff made by defiberizing and air laying into pad form the product of claim 1.

33. The disposable absorbent product of claim 31 comprising an absorbent core portion of which at least a portion is formed from the product of claim 1 in sheeted form.

34. A disposable absorbent product of claim 28 in which the absorbent core is further in admixture with a superabsorbent polymer.

35. A disposable absorbent product of claims 31 in which the absorbent core is further in admixture with a superabsorbent polymer.

36. The disposable absorbent of product claims 28, 29, 30, 31, 32, 33, 34, or 35 in which the product is a diaper.

37. The disposable absorbent product of claims 28, 29, 30, 31, 32, 33, 34, or 35 in which the product is a sanitary napkin.

38. A disposable absorbent product having an absorbent core portion comprising a readily debonded cellulose product as described in claim 1 in which said readily debonded product is in admixture with 10–90% by weight of other fibers selected from the group consisting of cellulosic fibers, chemically modified cellulose fibers and noncellulosic fibers.

39. The disposable absorbent product of claim 38 comprising an absorbent core portion formed of fluff made by defiberizing and air laying into pad form the product of claim 1.

40. The disposable absorbent product of claim 38 comprising an absorbent core portion of which at least a portion is formed from the product of claim 1 in sheeted form.

41. A disposable absorbent product having an absorbent core portion comprising a readily debonded cellulose product as described in claim 10 in which said readily debonded product is in admixture with 10–90% by weight of other fibers selected from the group consisting of cellulosic fibers, chemically modified cellulose fibers and noncellulosic fibers.

42. The disposable absorbent product of claim 41 comprising an absorbent core portion formed of fluff made by defiberizing and air laying into pad form the product of claim 10.

43. The disposable absorbent product of claim 41 comprising an absorbent core portion of which at least a portion is formed from the product of claim 10 in sheeted form.

44. A disposable absorbent product of claim 38 in which the absorbent core is further in admixture with a superabsorbent polymer.

45. A disposable absorbent product of claim 41 in which the absorbent core is further in admixture with a superabsorbent polymer.

46. The disposable absorbent of product claims 38, 39, 40, 41, 42, 43, 44, or 45 in which the product is a diaper.

47. The disposable absorbent product of claims 38, 39, 40, 41, 42, 43, 44, or 45 in which the product is a sanitary napkin.

* * * * *